United States Patent [19]
Chamontin et al.

[11] Patent Number: 6,136,968
[45] Date of Patent: Oct. 24, 2000

[54] HOMOAZAADAMANTANE SPIROOXAZINES AND THEIR USE IN THE FIELD OF OPHTHALMIC OPTICS

[75] Inventors: Karine Chamontin; Vladimir Lokshin; André Samat; Robert Guglielmetti, all of Marseilles, France

[73] Assignee: Transitions Optical Inc., Pinellas Park, Fla.

[21] Appl. No.: 09/230,672

[22] PCT Filed: Jul. 3, 1997

[86] PCT No.: PCT/FR97/01196

§ 371 Date: Jan. 29, 1999

§ 102(e) Date: Jan. 29, 1999

[87] PCT Pub. No.: WO98/04563

PCT Pub. Date: Feb. 5, 1998

[30] Foreign Application Priority Data

Jul. 31, 1996 [FR] France .................... 96 09659

[51] Int. Cl.[7] ............... C07D 498/10; G03C 1/685
[52] U.S. Cl. ............ 540/581; 540/580; 351/163; 252/586
[58] Field of Search ................ 540/580, 581; 351/163

[56] References Cited

U.S. PATENT DOCUMENTS

| 4,913,544 | 4/1990 | Rickwood et al. ............... 351/163 |
| 5,186,867 | 2/1993 | Castaldi et al. .................. 252/586 |

FOREIGN PATENT DOCUMENTS

| 0388660 | 9/1990 | European Pat. Off. . |
| 0449669 | 10/1991 | European Pat. Off. . |
| 0489655 | 6/1992 | European Pat. Off. . |
| 0653428 | 5/1995 | European Pat. Off. . |
| WO 96/04590 | 2/1996 | WIPO . |
| WO 96/11926 | 5/1996 | WIPO . |

*Primary Examiner*—Mukund J. Shah
*Assistant Examiner*—Pavanaram K Sripada
*Attorney, Agent, or Firm*—Frank P. Mallak

[57] ABSTRACT

Described are novel reversible photochromic compounds of the homoazaadamantane spirooxazine family. Certain substituents are present on the nitrogen atom of the homoazaadamantane portion of the compound and on the benzene ring fused to the oxazine portion of the compound. These compounds may be represented by the following formula:

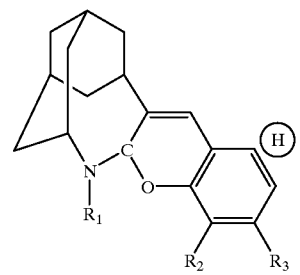

Also described are compositions, e.g., solvent based mediums and polymerized organic materials, used to produce ophthalmic components, that contain the homoazaadamantane compounds with or without other photochromic compounds.

17 Claims, No Drawings

HOMOAZAADAMANTANE SPIROOXAZINES AND THEIR USE IN THE FIELD OF OPHTHALMIC OPTICS

This application is a International 371 of PCT Application No. PCT/FR97/01196 filed Jul. 3, 1997.

The invention relates to novel photochromic compounds, more particularly photochromic compounds of the homoazaadamantane spirooxazine family, to their use in the field of ophthalmic optics, in particular in and/or on ophthalmic lenses, and to lenses for optical equipment.

The phenomenon of photochromism has been known for many years. A compound is said to be photochromic when, after irradiation with a light beam certain wavelengths of which are situated in the ultraviolet range, this compound changes color and returns to its original color once the irradiation is stopped.

This phenomenon has many applications, but one of the more particularly advantageous known applications relates to the field of ophthalmic optics.

Such compounds may be used in the production of lenses or glass for spectacles in order to filter light radiations depending on their intensity.

By incorporating photochromic compounds into an organic material constituting an ophthalmic lens, it is possible to obtain a glass of considerably reduced weight relative to conventional lenses made of inorganic glass which contain silver halides as photochromic agent. Their incorporation into organic materials has always posed technical difficulties.

However, not all compounds with photochromic properties are necessarily usable in the field of ophthalmic optics. Indeed, the photochromic compound must fulfill a certain number of criteria, some of which are:

strong colorability, which is a measurement of the capacity of a photochromic compound to show an intense color after isomerization;

coloration after absorption of light, which renders the photochromic compound capable of being used, alone or in combination with other photochromic compounds, in ophthalmic glass or lenses;

an absence of coloration, or very little coloration, in the initial form;

rapid coloration or decoloration kinetics;

photochromism exhibited in the widest possible temperature range, and in particular preferably between 0 and 40° C.

The organic photochromic compounds currently known and used generally show decreasing photochromism as the temperature rises, such that the photochromism is particularly pronounced at temperatures close to 0° C., whereas it is much weaker, or even nonexistent, at temperatures of the order of 40° C., which are temperatures which the glass may reach especially on exposure to the sun.

Another problem encountered by the photochromic compounds of the state of the art is their lifetime. Indeed, for certain products of the state of the art, a relatively short lifetime is observed. In effect, after a certain number of coloration and decoloration cycles, the photochromic compound undergoes chemical degradation and no longer displays reversible photochromic properties.

Document EP-A-0,338,660 describes photochromic compounds of the spiro[3H-1,4-oxazine] family comprising a piperidine type ring grafted onto the spiran carbon. These compounds have satisfactory photochromic characteristics with, in particular a hypsochromic shift of the absorption wavelength in the visible range compared with the standard spiro[indolinenaphthoxazine] reference series. On the other hand, the synthesis of compounds from document EP-A-033,660 proves to be difficult, in particular as regards the piperidine precursor.

It would be desirable to prepare photochromic compounds having higher spectrokinetic constants and consequently better photochromic properties, and which are easy to synthesize.

The Applicant Company has discovered a novel family of spirooxazines which show particularly advantageous photochromic properties. Indeed, the compounds in accordance with the invention show strong colorability, especially in the pink or gray/green range, which is particularly useful for ophthalmic optics, these compounds therefore capable of being used with photochromic compounds giving a yellow or red color such as chromenes with a view to obtaining a natural final coloration on exposure to light.

Furthermore, the compounds in accordance with the invention have no coloration, or very little coloration, in the initial state and show rapid coloration and decoloration kinetics across a very broad temperature range, between 0 and 40° C. in particular.

Furthermore, the compounds in accordance with the invention are easier to synthesize than the compounds of document EP-A-0,338,660.

The Applicant has also observed that these compounds had a particularly long lifetime.

The effect of all these properties is that these novel photochromic compounds are particularly advantageous in their use in ophthalmic optics and in particular for their use in and/or on ophthalmic lenses and optical equipment.

For the purposes of the invention, ophthalmic lenses refer to the glass of spectacles, in particular of sunglasses and contact lenses.

One subject of the invention thus consists of the novel photochromic compounds.

Another subject of the invention consists of the use thereof in ophthalmic optics.

The invention also relates to compositions intended to be used for coating ophthalmic lenses or to their incorporation into these lenses, and to lenses for optical equipment.

Other subjects of the invention will become apparent on reading the description and the examples which follow.

The photochromic compounds in accordance with the invention are essentially characterized in that they correspond to the general formula:

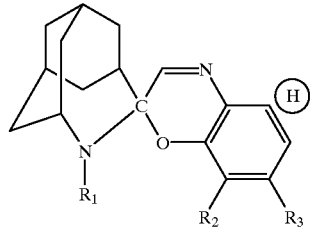

(I)

in which:

$R_1$ represents a $C_1$–$C_{16}$ alkyl group optionally substituted with one or more hydroxyl, halogen, aryl, alkoxy, acyloxy, acryloxy, methacryloxy or vinyl substituents; a vinyl, allyl, phenyl or arylalkyl group, a phenyl group mono- or disubstituted with $C_1$–$C_6$ alkyl or alkoxy or halogen substituents, an optionally substituted alicyclic group, or an aliphatic hydrocarbon group containing in its chain one or more hetero atoms chosen from O, N and S;

R$_2$ and R$_3$ denote, independently of each other, a hydrogen atom; an alkyl group; an aryl group; a group —(CH$_2$)$_m$OR, —SR, —COR or —COOR, in which R denotes a hydrogen atom, an alkyl group or an aryl group and m is an integer from 0 to 10; an amino group of formula NR$_4$R$_5$ in which R$_4$ and R$_5$ denote, independently of each other, a hydrogen atom, an alkyl group, a cycloalkyl group, an aryl group, it being possible for R$_4$ and R$_5$ to form, with the nitrogen atom, a 4- to 7-membered heterocycle which can also contain one or more endocyclic hetero atoms chosen from nitrogen, oxygen and sulfur; a halogen atom; a mono- or polyhaloalkyl group; an —NO$_2$, —CN or —SCN group, a group SO$_3$R' in which R' denotes hydrogen or an alkali metal, a group SO$_2$R" in which R" is a phenyl or tolyl group; or an acrylic, methacrylic, vinyl or allylic polymerizable group optionally containing a long chain, for example a linear or branched C$_1$–C$_{12}$ alkyl group optionally interrupted by one or more oxygen atoms or carboxyl groups containing at least one acrylic, methacrylic, vinyl or allylic group, preferably at the end of the chain; H is a 4- to 7-membered and preferably 5- or 6-membered aromatic heterocycle or an aromatic hydrocarbon-based ring, the heterocycle containing one or more endocyclic hetero atoms chosen from nitrogen, oxygen and sulfur, it being possible for these rings and heterocycles to be substituted with one or more groups as defined for R$_2$ and R$_3$ or fused with an aromatic or cycloalkyl ring.

In the abovementioned formula, an alkyl group preferably denotes a group having 1 to 6 carbon atoms, a cycloalkyl group preferably denotes a group having 3 to 7 carbon atoms, the aryl group preferably denotes a phenyl group, halogen preferably denotes chlorine, bromine or fluorine, and the polyhaloalkyl group preferably denotes the CF$_3$ group.

Among the alkyl groups represented by R$_1$, mention may be made of methyl, ethyl, n-propyl, isopropyl and n-butyl groups.

Among the arylalkyl groups, R$_1$ preferably represents the benzyl group.

The aromatic heterocycle H is represented more particularly by formula (II):

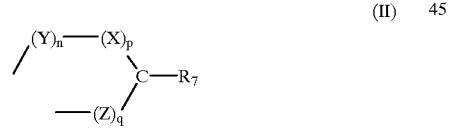

(II)

in which:

X, Y and Z denote, independently of each other, a group CR$_6$ in which R$_6$ represents hydrogen, a C$_1$–C$_6$ alkyl group or a phenyl group, the carbon atom being linked to one of the neighboring atoms via a double bond; a nitrogen atom linked to one of the neighboring atoms via a double bond; an oxygen or sulfur atom; n, p and q being integers equal to 0 or 1;

R$_7$ denotes hydrogen, a a C$_1$–C$_6$ alkyl group or a phenyl group, or R$_7$ and X or R$_7$ and Z together possibly forming a 5- or 6-membered aromatic or nonaromatic ring, preferably a benzene ring, or a naphthalene ring-system, optionally substituted with one or more groups (R$_8$)$_r$, R$_8$ having the meaning of any one of the groups R$_1$, R$_2$ and R$_3$ as defined above and r having an integer value from 1 to 4 when this system is a benzene ring or from 1 to 6 when this system is a naphthalene ring-system; X, Y, Z and CR$_7$ being chosen so as to ensure the aromaticity of the heterocycle fused to the naphthoxazine ring-system.

The heterocyclic rings particularly preferred are chosen from the groups of formula (II) in which n is equal to 0, X denotes O, S or N and Z denotes CR$_7$ or X denotes CR$_7$ and Z denotes O, S or N, R$_6$ and R$_7$ having the meanings indicated above. X preferably denotes O or S.

Other preferred compounds are those for which n+p+q=3 and at least one of the groups X, Y or Z denotes N.

Among the aromatic rings which can be represented by H, mention may be made of benzene, hydroxybenzenes, alkoxybenzenes such as methoxybenzene, and halobenzenes such as bromobenzene. Among the aromatic heterocycles which can be represented by H, mention may be made of thiophene, benzothiophene, naphthothiophene, furan, pyran, isobenzofuran, pyrrole, imidazole, pyrazole, isothiazole, isoxazole, pyridine, pyrazine, pyrimidine, pyridazine, isoindole, indole, indazole, isoquinoline, quinoline, phthalazine, quinoxaline, quinazoline and cinnaline, it being optionally possible for these rings to contain one or more substituents.

The heterocyclic rings H more particularly preferred are chosen from pyridine, pyrimidine, pyrazine and furan rings optionally fused with an aromatic ring to form an optionally substituted benzofuran or thiazole ring-system.

Preferred photochromic compounds according to the invention correspond to the formulae:

(III)

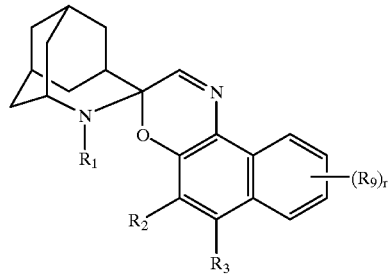

(IV)

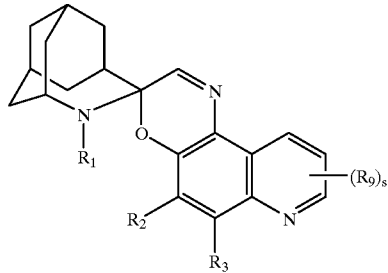

(V)

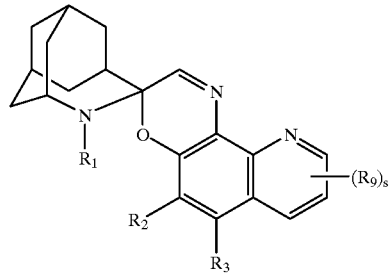

(VI)

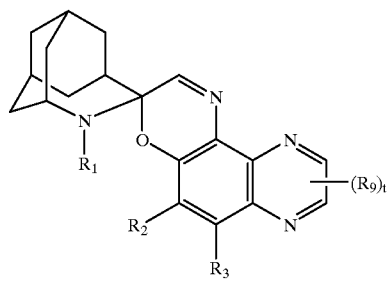

(VII)

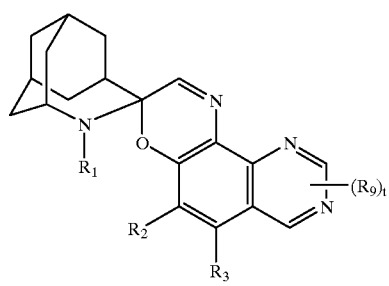

(VIII)

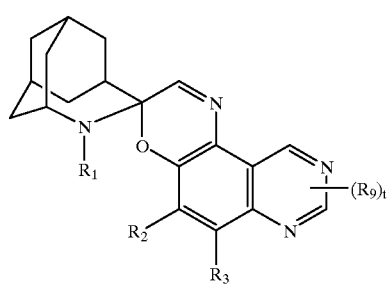

(IX)

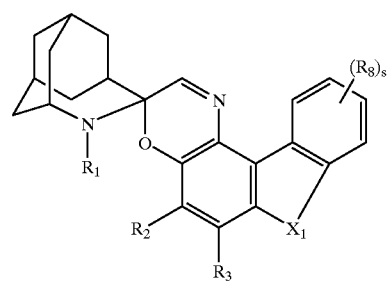

(X)

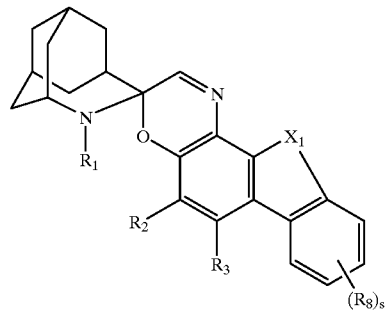

in which $R_1$, $R_2$, $R_3$ and $R_8$ have the same meaning as above, $R_9$ is a group as defined for $R_2$ and $R_3$, $X_1$ represents —S— or —O—, r is an integer from 0 to 4, s is an integer from 0 to 3 and t is equal to 0, 1 or 2.

The novel compounds according to the invention can be synthesized easily using the process described in J. Org. Chem. 43, 20, 1978.

The reaction scheme is indicated below.

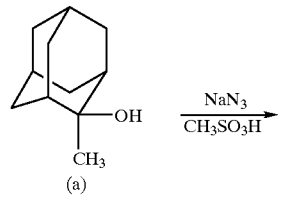

(a)

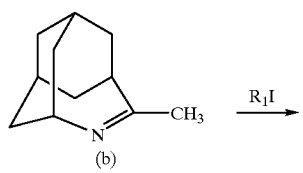

(b)

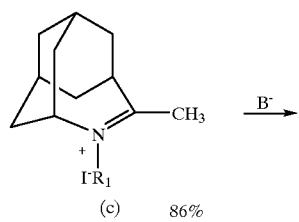

(c)   86%

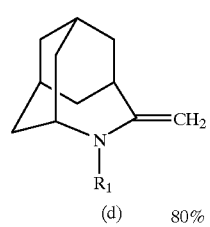

(d)   80%

A substituted nitrosonaphthol or a substituted aminonaphthol is reacted with the quaternary base c), in the presence of triethylamine, or with the methylenic base d), according to the reaction scheme below.

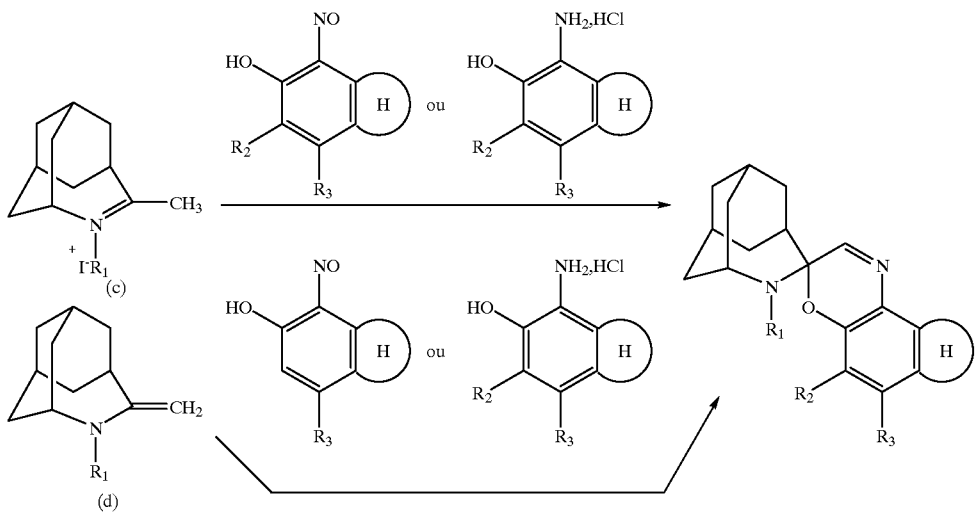

The photochromic compounds in accordance with the invention may be used to produce photochromic ophthalmic lenses.

The compounds in accordance with the invention may be introduced into a composition which is intended to be applied to or introduced into a transparent organic polymer material in order to obtain a transparent photochromic article. They may also be introduced into solid compositions such as plastic films, sheets and lenses in order to produce materials which may especially be used as ophthalmic lenses, sunglasses, visors, camera optics and filters.

The liquid compositions which constitute one subject of the invention are essentially characterized in that they contain the compounds in accordance with the invention in dissolved or dispersed form in a solvent-based medium which are suitable for application to or introduction into a transparent polymer material.

Solvents which may more particularly be used are organic solvents chosen from benzene, toluene, chloroform, ethyl acetate, methyl ethyl ketone, acetone, ethyl alcohol, methyl alcohol, acetonitrile, tetrahydrofuran, dioxane, ethylene glycol methyl ether, dimethylformamide, dimethyl sulfoxide, methylcellosolve, morpholine and ethylene glycol.

When the compounds in accordance with the invention are dispersed, the medium may also contain water.

According to another embodiment, the compounds in accordance with the invention may be introduced into, and preferably dissolved in, colorless or transparent solutions prepared from transparent polymers, transparent copolymers or mixtures of transparent polymers in a suitable organic solvent.

Examples of such solutions are, inter alia, solutions of nitrocellulose in acetonitrile, of polyvinyl acetate in acetone, of polyvinyl chloride in methyl ethyl ketone, of polymethyl methacrylate in acetone, of cellulose acetate in dimethylformamide, of polyvinylpyrrolidone in acetonitrile, of polystyrene in benzene, and of ethylcellulose in methylene chloride.

These compositions may be applied to transparent supports, such as supports made of polyethylene glycol terephthalate, of borylated paper, or of cellulose triacetate, and dried in order to obtain a photochromic material, which may become colored in the presence of ultraviolet radiation and which returns to the colorless and transparent state in the absence of the source of radiation.

The photochromic compounds of the present invention, or the compositions containing them, which are defined above may be applied to or incorporated into a solid transparent polymerized organic material which is suitable for ophthalmic components such as ophthalmic lenses, or into useful materials which may be used in sunglasses, visors, camera optics and filters.

By way of solid transparent materials which may be used to produce ophthalmic lenses in accordance with the invention, there may be mentioned polyol(allyl carbonate) polymers, polyacrylates, poly(alkyl acrylate)s such as polymethyl methacrylates, cellulose acetate, cellulose triacetate, cellulose acetate propionate, cellulose acetate butyrate, poly (vinyl acetate), poly(vinyl alcohol), polyurethanes, polycarbonates, polyethylene-terephthalates, polystyrenes, poly(styrene-methyl methacrylate)s, copolymers of styrene and acrylonitrile, and polyvinyl butyrates.

The transparent copolymers or mixtures of transparent polymers are also suitable for producing such materials.

There may be mentioned, in this respect, materials prepared from polycarbonates, such as poly(4,4'-dioxy-2,2-diphenylpropane), polymethyl methacrylate, polyol(allyl carbonate)s, in particular such as diethylene glycol bis(allyl carbonate) and the copolymers thereof, for example such as with vinyl acetate. The copolymers of diethylene glycol bis(allyl carbonate) and of vinyl acetate (80–90/10–20) may be mentioned in particular, and also the copolymer of diethylene glycol bis(allyl carbonate) with vinyl acetate, cellulose acetate and cellulose propionate, and cellulose butyrate (80–85/15–20).

The polyol(allyl carbonate)s are prepared using the allyl carbonates of linear or branched, aliphatic or aromatic liquid polyols, such as aliphatic bis(allyl carbonate) glycols or alkylene bis(allyl carbonate)s. Among the polyol(allyl carbonate)s that can be used to prepare the solid transparent materials which may be used in accordance with the invention, there may be mentioned ethylene glycol bis(allyl carbonate), diethylene glycol bis(2-methallyl carbonate), diethylene glycol bis(allyl carbonate), ethylene glycol bis (2-chloroallyl carbonate), triethylene glycol bis(allyl carbonate), 1,3-propanediol bis(allyl carbonate), propylene glycol bis(2-ethylallyl carbonate), 1,3-butanediol bis(allyl carbonate), 1,4-butanediol bis(2-bromoallyl carbonate), dipropylene glycol bis(allyl carbonate), trimethylene glycol bis(2-ethylallyl carbonate), pentamethylene glycol bis(allyl carbonate), and isopropylenebisphenol bis(allyl carbonate). The most important product consists of diethylene glycol bis(allyl carbonate), also known under the name CR39.

The amount of photochromic compounds to be used in accordance with the invention, either in the composition or at the time of its introduction into the solid support, is not critical and generally depends on the intensity of the color that the composition may impart to the material after exposure to radiation. Generally speaking, the more photochromic compounds are added, the more intense will be the coloration under irradiation.

In accordance with the invention, an amount is used which is sufficient to impart to the treated material the property of changing color at the time of exposure to radiation. This amount of photochromic compounds is generally between 0.01 and 20% by weight, and preferably between 0.05 and 10% by weight, relative to the total weight of the optical material or of the composition.

The photochromic compounds in accordance with the invention may also be introduced into a temporary transfer support (such as a varnish which forms a coating on a substrate) and then be thermally transferred into the substrate, as described in particular in U.S. Pat. No. 4,286,957 or 4,880,667.

Thus, the invention also relates to a transfer varnish which contains at least one photochromic compound in accordance with the invention.

These compounds may be used with other photochromic compounds which are known in the state of the art, such as photochromic compounds giving rise to various colorations such as yellow and red. It is thus possible to use chromenes which are well known in the state of the art.

Once applied to ophthalmic materials or introduced into such materials, the appearance of a coloration is observed after exposure to UV irradiation and the return to the original color or to the original transparency is observed when the exposure to UV radiation is interrupted.

The compounds in accordance with the invention have the advantage of allowing this change in coloration to take place a large number of times and at very variable temperatures, of between 0 and 40° C.

The examples which follow are intended to illustrate the invention, but are not limiting in nature.

EXAMPLE 1

Preparation of the compound:

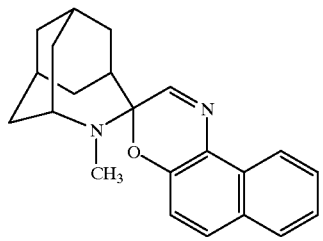

10 ml of toluene are added to a mixture containing 0.30 g (1 mmol) of compound c) for which $R_1=CH_3$, 0.22 g (1.1 mmol) of aminonaphthol hydrochloride,

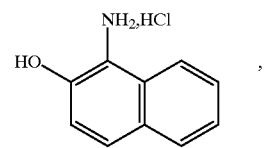

0.4 g of sodium hydrogen carbonate, 0.15 g (1.25 mmol) of dimethyl sulfoxide and 0.25 g (2.5 mmol) of triethylamine, and the mixture is left at 50° C. for 5 hours. The mixture is filtered and washed with hot toluene (5 ml) and the filtrate is evaporated. The product is then purified by flash chromatography (95 hexane/5 ethyl acetate).

The expected product is obtained with a melting point of 108° C., in a yield of 26%.

EXAMPLE 2

Preparation of the compound:

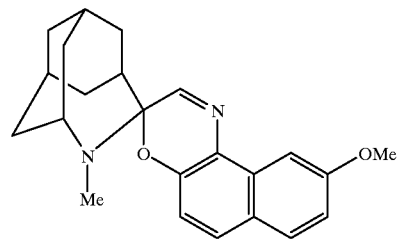

10 ml of toluene are added to a mixture of 0.17 g (1 mmol) of the compound of formula (d) in which $R_1=CH_3$, 0.22 g (1.1 mmol) of aminonaphthol hydrochloride, 0.4 g of sodium hydrogen carbonate, 0.15 g (1.25 mmol) of dimethyl sulfoxide and 0.15 g (1.5 mmol) of triethylamine, and the mixture is left at 50° C. for 5 hours. The mixture is filtered and washed with hot toluene (5 ml) and the filtrate is evaporated. The product is then purified by flash chromatography (95 pentane/5 ethyl acetate).

The expected product is obtained with a melting point of 159° C., in a yield of 32%.

EXAMPLE 3

Preparation of the compound:

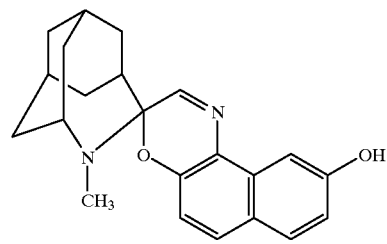

15 ml of ethanol are added to a mixture of 0.30 g (1 mmol) of compound (c) in which $R_1=CH_3$, 0.19 g (1 mmol) of 1-nitroso-2,7-dihydroxynaphthalene and 0.12 g (1.2 mmol) of triethylamine, and the mixture is refluxed for 4 hours. The solvent is evaporated off. The product is purified by flash chromatography (80 pentane/20 ethyl acetate).

The expected product is obtained with a melting point of 188° C., in a yield of 29%.

EXAMPLE 4

Preparation of the compound:

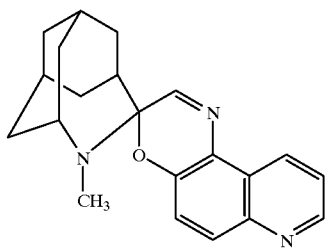

15 ml of trichloroethylene are added to a mixture of 0.17 g (1 mmol) of compound (d) for which $R_1=CH_3$, 0.17 g (1 mmol) of 6-hydroxy-5-nitrosoquinoline and 0.12 g (1.2 mmol) of triethylamine, and the mixture is refluxed for 3 hours. The solvent is evaporated off. The product is then purified by flash chromatography (90 dichloromethane/10 ethyl acetate).

The expected product is obtained with a melting point of 101° C., in a yield of 24%.

EXAMPLE 5

Preparation of the compound:

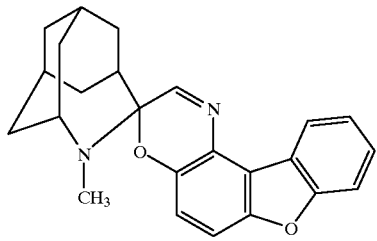

This compound is obtained as in Example 3, starting with compound (c) ($R_1=CH_3$) and 3-hydroxy-4-nitrosodibenzofuran.

The expected product is obtained with a melting point of 122° C., in a yield of 12%.

EXAMPLE 6

Preparation of the compound:

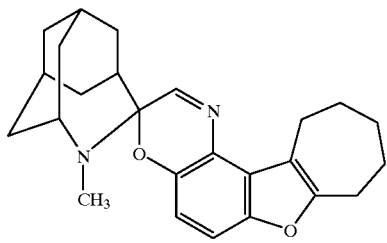

This compound is obtained as in Example 3, starting with compound (c) ($R_1=CH_3$) and 5-hydroxy-4-nitroso-2,3-pentamethylenebenzofuran.

The expected product is obtained with a melting point of 81° C., in a yield of 22%.

EXAMPLE 7

Preparation of the compound:

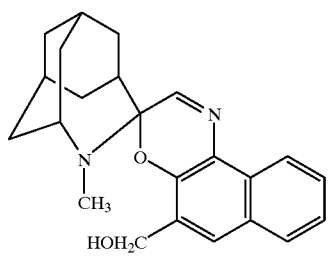

This compound is obtained as in Example 3, starting with compound (c) ($R_1=CH_3$) and 3-hydroxymethyl-1-nitroso-2-naphthol.

The expected product is obtained with a melting point of 128° C., in a yield of 28%.

EXAMPLE 8

Preparation of the compound:

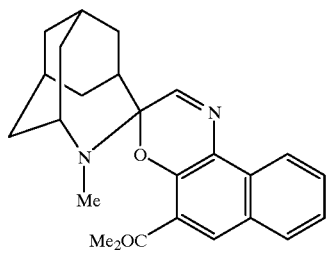

This compound is obtained as in Example 3, starting with compound (c) ($R_1=CH_3$) and 3-methoxycarbonyl-1-nitroso-2-naphthol.

The expected product is obtained with a melting point of 92° C., in a yield of 16%.

EXAMPLE 9

Preparation of the compound:

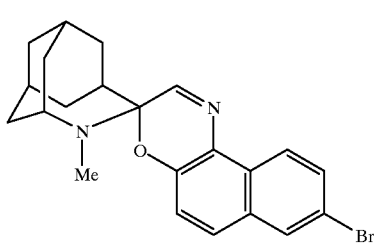

This compound is obtained as in Example 3, starting with compound (c) ($R_1=CH_3$) and 6-bromo-1-nitroso-2-naphthol.

The expected product is obtained with a melting point of 115° C., in a yield of 14%.

EXAMPLE 10

Preparation of the compound:

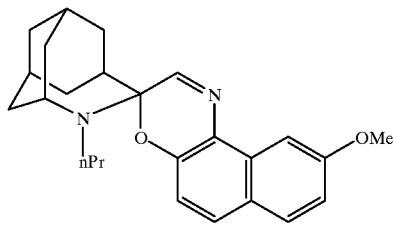

This compound is obtained as in Example 3, starting with compound (c) ($R_1$=nPr) and 7-methoxy-1-nitroso-2-naphthol.

The expected product is obtained with a melting point of 106° C., in a yield of 18%.

COMPARATIVE EXAMPLES 11 and 12

The compounds of the Comparative Examples 11 and 12 were synthesized according to the references below, in order to compare them with the products of the present invention.

The reaction scheme is as follows:

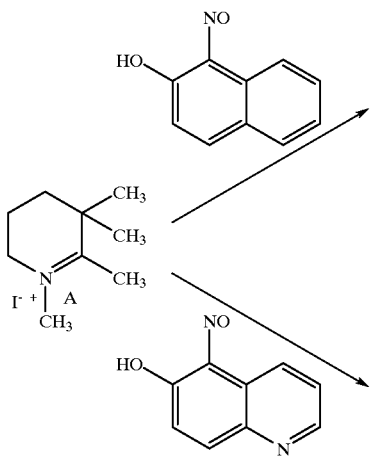

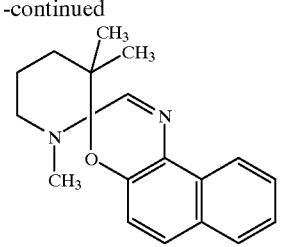

10%

11

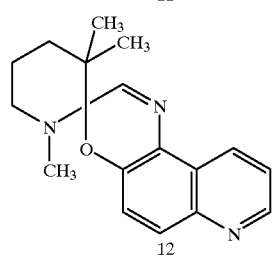

2%

12

The synthesis of compound 11 is more particularly described in Bull. Chem. Soc. Jpn, 63, 267–268, 1990 and that of compound 12 in patent EP-A-0,388,660.

The syntheses of product A described in the patents EP-A-0,358,774 and U.S. Pat. No. 4,287,337 (R. Guglielmetti) bear witness to the difficulty in gaining access to this compound.

The spectrokinetic parameters of the products of Examples 1–10 and of the comparative products 11 and 12 ($A_0$, K and $\lambda_{max}$) (K denotes the thermal decolorization rate constant and $A_0$ denotes the "colorability" determined by the absorbance value measured directly after the flash of irradiation) were obtained by flash photolysis coupled to a rapid spectrometer of the Warner and Swasey type. The experimental conditions are as described in patent application WO 96/04590, in particular using photochrome concentrations of $2.5\times10^{-5}$ M.$l^{-1}$ in toluene and a temperature of 25° C.

The results are indicated in Table I below.

| Product | λ_max (nm) * | Thermal decolorization kinetic constant K (s$^{-1}$) | Colorability A$_0$ | Color |
|---|---|---|---|---|
| 1 | 544 580 | K = 0.092 | 0.96 | pink |
| 2 | 538 574 | K = 0.130 | 0.84 | pink |
| 3 | 538 574 | K = 0.130 | 0.98 | pink |
| 4 | 538 574 | K = 0.036 | 1.08 (absorbs av the flash) | pink |
| 5 | 452 600 | K = 0.012 | 0.36 | green-gray |

-continued
| Product | $\lambda_{max}$ (nm) * | Thermal decolorization kinetic constant $K$ (s$^{-1}$) | Colorability $A_0$ | Color |
|---|---|---|---|---|
| 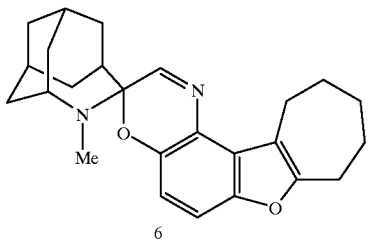　6 | <u>474</u><br>590 | $K = 0.12$ | 0.46 | green-gray |
*The values underlined correspond to the bands of strongest intensity
| Product | $\lambda_{max}$ (nm) * | Thermal decolorization kinetic constant $K$ (s$^{-1}$) | Colorability $A_0$ | Color |
|---|---|---|---|---|
| 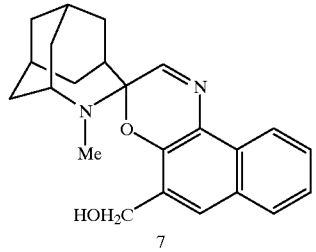　7 | <u>580</u><br>547 | $K = 0.037$ | 0.80 | pink |
| 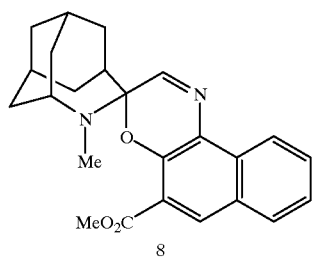　8 | <u>590</u><br>555 | $K = 0.044$ | 1.09 | pink |

-continued

| Product | $\lambda_{max}$ (nm) * | Thermal decolorization kinetic constant $K$ (s$^{-1}$) | Colorability $A_0$ | Color |
|---|---|---|---|---|
| 9 | 582 546 | K = 0.043 | 0.66 | pink |
| 10 | 575 541 | K = 0.044 | 0.85 | pink |
| 11 | 582 547 | K = 5.400 | 0.44 | pink |
| 12 | 575 542 | K = 0.980 | 0.46 | pink |

*The values underlined correspond to the bands of strongest intensity

On account of the relatively low colorability and the rapid rate of decolorization, the photochromism of the products of Comparative Examples 11 and 12 is undetectable at room temperature in toluene.

EXAMPLE 13

Compounds 1, 2, 11 and 12 were tested in a polymer matrix, prepared in the following way:

A solution containing 10% by weight of polymethyl methacrylate (PMMA), obtained from the company Aldrich, and 3% by weight of photochrome in chloroform is prepared. The solution is deposited as a thin layer in a crystallizing dish. The solvent is left to evaporate off and the plastic film is then detached.

The photochromism of the films thus obtained was observed under (flash) UV irradiation.

Products 1 and 2 give good coloration. Product 11 shows no coloration. However, product 12 is photochromic under these conditions, with weaker colorability.

It emerges from the above examples that the colorability values $A_0$ of the compounds according to the invention are better than those of the compounds of Comparative Examples 11 and 12 and the values of the kinetic constants are lower.

In addition, the synthesis of the homoazaadamantane portion of the compounds according to the invention is much easier than the synthesis of the piperidine portion of comparative examples 11 and 12 and the formation of the corresponding spirooxazines of the invention consequently proves to be more efficient.

What is claimed is:

1. A photochromic compound of formula:

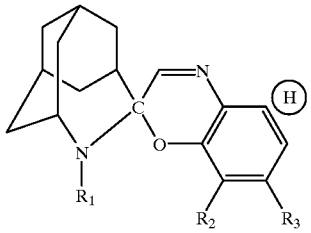
(I)

in which:

R₁ represents a $C_1$–$C_{16}$ alkyl group optionally substituted with one or more hydroxyl, halogen, aryl, alkoxy, acyloxy, acryloxy, methacryloxy or vinyl substituents; a vinyl, allyl, phenyl or arylalkyl group, a phenyl group mono- or disubstituted with $C_1$–$C_6$ alkyl or alkoxy or halogen substituents, an optionally substituted alicyclic group, or an aliphatic hydrocarbon group containing in its chain or more hetero atoms chosen from O, N and S;

R₂ and R₃ denote, independently of each other, a hydrogen atom; an alkyl group; an aryl group; a group —(CH₂)$_m$OR, —SR, —COR or —COOR, in which R denotes a hydrogen atom, an alkyl group or an aryl group and m is an integer from 0 to 10; an amino group of formula NR₄R₅ in which R₄ and R₅ denote, independently of each other, a hydrogen atom, an alkyl group, a cycloalkyl group, an aryl group, it being possible for R₄ and R₅ to form, with the nitrogen atom, a 4- to 7-membered heterocycle which can also contain one or more endocyclic hetero atoms chosen from nitrogen, oxygen and sulfur; a halogen atom; a mono- or polyhaloalkyl group; an —NO₂, —CN or —SCN group; a group SO₃R' in which R' denotes hydrogen or an alkali metal, a group SO₂R" in which R" is a phenyl or tolyl group; or an acrylic, methacrylic, vinyl or allylic polymerizable group optionally containing a long chain; H is a 4- to 7-membered and preferably 5- or 6-membered aromatic heterocycle or an aromatic hydrocarbon-based ring, the heterocycle containing one or more endocyclic hetero atoms chosen from nitrogen, oxygen and sulfur, it being possible for these rings and heterocycles to be substituted with one or more groups as defined for R₂ and R₃, fused with an aromatic or cycloalkyl ring.

2. The compound of claim 1, wherein the ring or the heterocycle H is a 5- or 6-membered ring.

3. The compound of claim 1, wherein the aromatic heterocycle corresponds to the general formula:

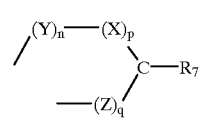
(II)

in which:

X, Y and Z denote, independently of each other, a group CR₆ in which R₆ represents hydrogen, a $C_1$–$C_6$ alkyl group or a phenyl group, or R₇ and X or R₇ and Z together possibly forming a 5- or 6-membered aromatic or nonaromatic ring, preferably a benzene ring, or a naphthalene ring-system, optionally substituted with one or more groups (R₈)$_r$, R₈ having the meaning of any one of the groups R₁, R₂ and R₃ as defined above, and r having an integer value from 1 to 4 when this system is a benzene ring or from 1 to 6 when this system is a naphthalene ring-system; X, Y, Z and CR₇ being chosen so as to ensure the aromaticity of the heterocycle fused to the naphthoxazine ring-system.

4. The compound of claim 3, wherein the group of formula (II), n is equal to 0, X denotes O, S or N, and Z denotes CR₇, or alternatively X denotes CR₇ and Z denotes O, S or N, R₆ and R₇ having the meanings indicated in claim 3.

5. The compound of claim 3, wherein n+p+q=3 and at least one of the groups X, Y or Z denotes N.

6. The compound of claim 1, wherein the photochromic compounds are chosen from the compounds of formulae:

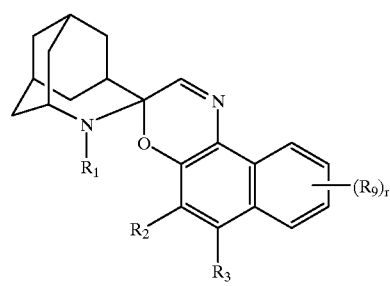
(III)

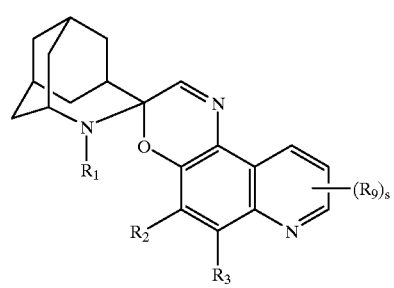
(IV)

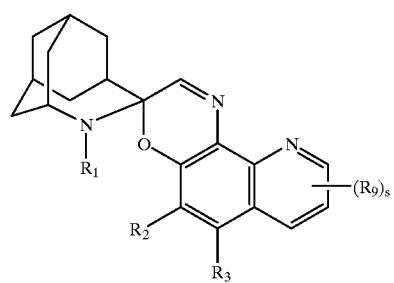
(V)

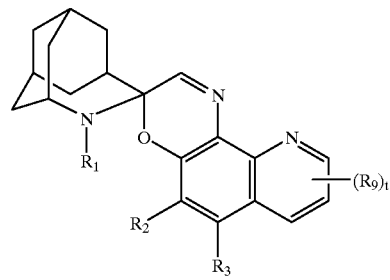
(VI)

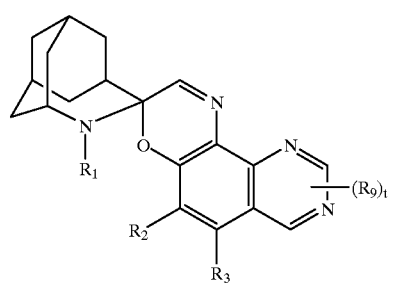
(VII)
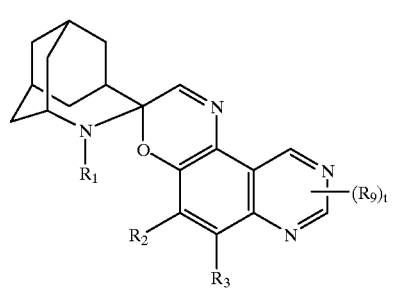
(VIII)
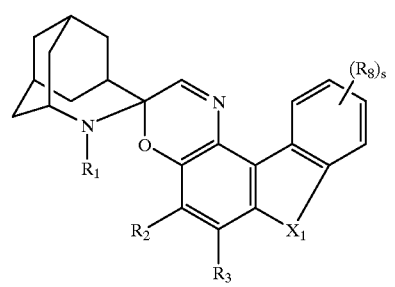
(IX)
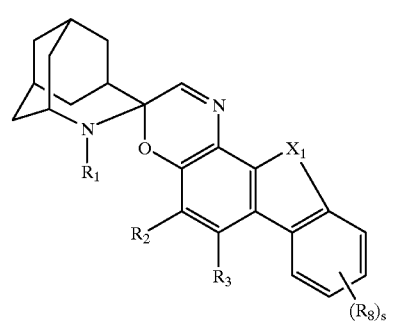
(X)
in which $R_1$, $R_2$, $R_3$ and $R_8$ have the same meaning as in claims 1 and 2, $R_9$ is a group as defined for $R_2$ and $R_3$, $X_1$ represents —S— or —O—, r is an integer from 0 to 4, s is an integer from 0 to 3, and t is equal to 0, 1 or 2.
7. The compound of claim 1, further defined as having the formula:
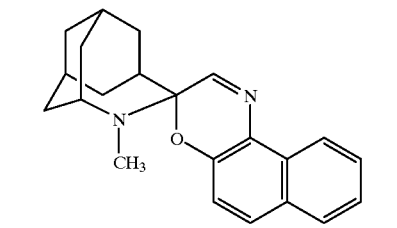
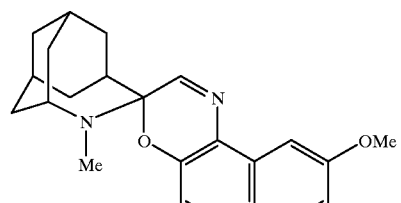
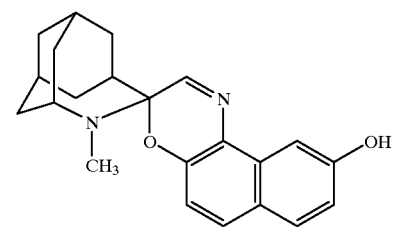
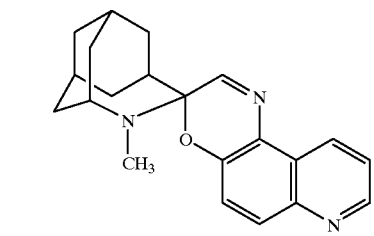
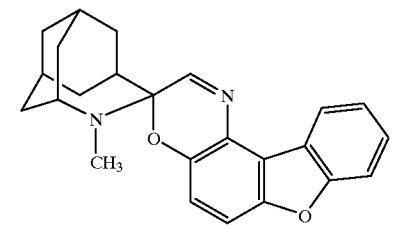
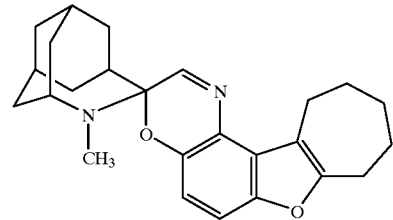
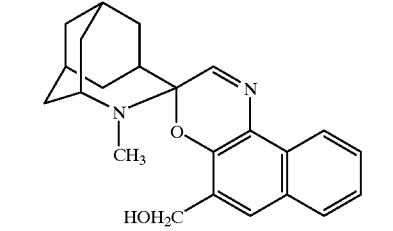

-continued

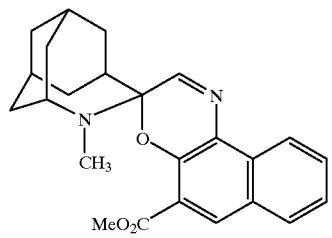

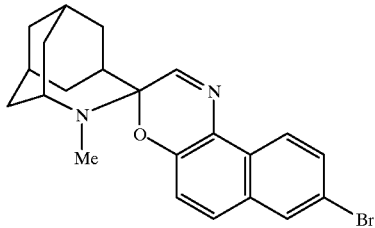

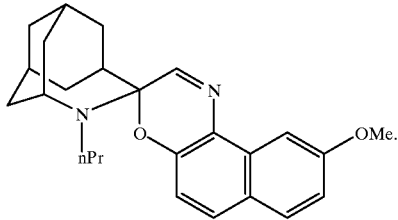

8. A method of making a photochromic composition comprising applying to or introducing into a trasperent organic polymer material at least one photochromic compound of formula:

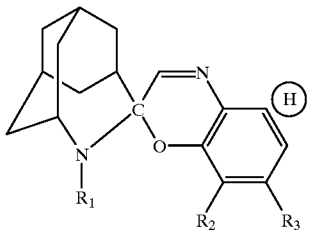

(I)

in which:

$R_1$ represents a $C_1$–$C_{16}$ alkyl group optionally substituted with one or more hydroxyl, halogen, aryl, alkoxy, acyloxy, acryloxy, methacryloxy or vinyl substituents; a vinyl, allyl, phenyl or arylalkyl group, a phenyl group mono- or disubstituted with $C_1$–$C_6$ alkyl or alkoxy or halogen substituents, an optionally substituted alicyclic group, or an aliphatic hydrocarbon group containing in its chain or more hetero atoms chosen from O, N and S;

$R_2$ and $R_3$ denote, independently of each other, a hydrogen atom; an alkyl group; an aryl group; a group —(CH$_2$)$_m$OR, —SR, —COR or —COOR, in which R denotes a hydrogen atom, an alkyl group or an aryl group and m is an integer from 0 to 10; an amino group of formula NR$_4$R$_5$ in which R$_4$ and R$_5$ denote, independently of each other, a hydrogen atom, an alkyl group, a cycloalkyl group, an aryl group, it being possible for R$_4$ and R$_5$ to form, with the nitrogen atom, a 4- to 7-membered heterocycle which can also contain one or more endocyclic hetero atoms chosen from nitrogen, oxygen and sulfur; a halogen atom; a mono- or polyhaloalkyl group; an —NO$_2$, —CN or —SCN group; a group SO$_3$R' in which R' denotes hydrogen or an alkali metal, a group SO$_2$R" in which R" is a phenyl or tolyl group; or an acrylic, methacrylic, vinyl or allylic polymerizable group optionally containing a long chain; H is a 4- to 7-membered and preferably 5- or 6-membered aromatic heterocycle or an aromatic hydrocarbon-based ring, the heterocycle containing one or more endocyclic hetero atoms chosen from nitrogen, oxygen and sulfur, it being possible for these rings and heterocycles to be substituted with one or more groups as defined for R$_2$ and R$_3$, fused with an aromatic or cycloalkyl ring.

9. A composition comprising, least one photochromic compound of formula:

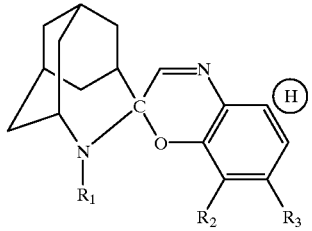

(I)

in which:

$R_1$ represents a $C_1$–$C_{16}$ alkyl group optionally substituted with one or more hydroxyl, halogen, aryl, alkoxy, acyloxy, acryloxy, methacryloxy or vinyl substituents; a vinyl, allyl, phenyl or arylalkyl group, a phenyl group mono- or disubstituted with $C_1$–$C_6$ alkyl or alkoxy or halogen substituents, an optionally substituted alicyclic group, or an aliphatic hydrocarbon group containing in its chain or more hetero atoms chosen from O, N and S;

$R_2$ and $R_3$ denote, independently of each other, a hydrogen atom; an alkyl group; an aryl group; a group —(CH$_2$)$_m$OR, —SR, —COR or —COOR, in which R denotes a hydrogen atom, an alkyl group or an aryl group and m is an integer from 0 to 10; an amino group of formula NR$_4$R$_5$ in which R$_4$ and R$_5$ denote, independently of each other, a hydrogen atom, an alkyl group, a cycloalkyl group, an aryl group, it being possible for R$_4$ and R$_5$ to form, with the nitrogen atom, a 4- to 7-membered heterocycle which can also contain one or more endocyclic hetero atoms chosen from nitrogen, oxygen and sulfur; a halogen atom; a mono- or polyhaloalkyl group; an —NO$_2$, —CN or —SCN group; a group SO$_3$R' in which R' denotes hydrogen or an alkali metal, a group SO$_2$R" in which R" is a phenyl or tolyl group; or an acrylic, methacrylic, vinyl or allylic polymerizable group optionally containing a long chain; H is a 4- to 7-membered and preferably 5- or 6-membered aromatic heterocycle or an aromatic hydrocarbon-based ring, the heterocycle containing one or more endocyclic hetero atoms chosen from nitrogen, oxygen and sulfur, it being possible for these rings and heterocycles to be substituted with one or more groups as defined for R$_2$ and R$_3$, fused with an aromatic or cycloalkyl ring.

10. The composition of claim 9, further defined as a liquid containing the photochromic compound dissolved or dispersed form in a solvent-based medium which are suitable for application to or introduction into a transparent polymer material.

11. The composition of claim 9, further comprising a second photochromic compound to give rise to different colorations.

12. A composition comprising a colorless or transparent solution based on transparent polymers, transparent copolymers, or a mixture of transparent polymers in a suitable organic solvent, and, in amounts sufficient to allow the material to change color once it has been exposed to ultraviolet radiation, a photochromic compound of formula:

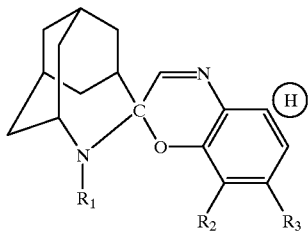

(I)

in which:
- $R_1$ represents a $C_1$–$C_{16}$ alkyl group optionally substituted with one or more hydroxyl, halogen, aryl, alkoxy, acyloxy, acryloxy, methacryloxy or vinyl substituents; a vinyl, allyl, phenyl or arylalkyl group, a phenyl group mono- or disubstituted with $C_1$–$C_6$ alkyl or alkoxy or halogen substituents, an optionally substituted alicyclic group, or an aliphatic hydrocarbon group containing in its chain or more hetero atoms chosen from O, N and S;
- $R_2$ and $R_3$ denote, independently of each other, a hydrogen atom; an alkyl group; an aryl group; a group —$(CH_2)_m OR$, —SR, —COR or —COOR, in which R denotes a hydrogen atom, an alkyl group or an aryl group and m is an integer from 0 to 10; an amino group of formula $NR_4R_5$ in which $R_4$ and $R_5$ denote, independently of each other, a hydrogen atom, an alkyl group, a cycloalkyl group, an aryl group, it being possible for $R_4$ and $R_5$ to form, with the nitrogen atom, a 4- to 7-membered heterocycle which can also contain one or more endocyclic hetero atoms chosen from nitrogen, oxygen and sulfur; a halogen atom; a mono- or polyhaloalkyl group; an —$NO_2$, —CN or —SCN group; a group $SO_3R'$ in which R' denotes hydrogen or an alkali metal, a group $SO_2R''$ in which R'' is a phenyl or tolyl group; or an acrylic, methacrylic, vinyl or allylic polymerizable group optionally containing a long chain; H is a 4- to 7-membered and preferably 5- or 6-membered aromatic heterocycle or an aromatic hydrocarbon-based ring, the heterocycle containing one or more endocyclic hetero atoms chosen from nitrogen, oxygen and sulfur, it being possible for these rings and heterocycles to be substituted with one or more groups as defined for $R_2$ and $R_3$, fused with an aromatic or cycloalkyl ring.

13. The composition of claim 12, further comprising a second photochromic compound to give rise to different colorations.

14. A transparent solid material comprising, in amounts sufficient to allow the material to change color once it has been exposed to ultraviolet radiation, a photochromic compound of formula:

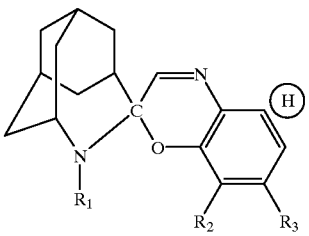

(I)

in which:
- $R_1$ represents a $C_1$–$C_{16}$ alkyl group optionally substituted with one or more hydroxyl, halogen, aryl, alkoxy, acyloxy, acryloxy, methacryloxy or vinyl substituents; a vinyl, allyl, phenyl or arylalkyl group, a phenyl group mono- or disubstituted with $C_1$–$C_6$ allyl or alkoxy or halogen substituents, an optionally substituted alicyclic group, or an aliphatic hydrocarbon group containing in its chain or more hetero atoms chosen from O, N and S;
- $R_2$ and $R_3$ denote, independently of each other, a hydrogen atom; an alkyl group; an aryl group; a group —$(CH_2)_m OR$, —SR, —COR or —COOR, in which R denotes a hydrogen atom, an alkyl group or an aryl group and m is an integer from 0 to 10; an amino group of formula $NR_4R_5$ in which $R_4$ and $R_5$ denote, independently of each other, a hydrogen atom, an alkyl group, a cycloalkyl group, an aryl group, it being possible for $R_4$ and $R_5$ to form, with the nitrogen atom, a 4- to 7-membered heterocycle which can also contain one or more endocyclic hetero atoms chosen from nitrogen, oxygen and sulfur; a halogen atom; a mono- or polyhaloalkyl group; an —$NO_2$, —CN or —SCN group; a group $SO_3R'$ in which R' denotes hydrogen or an alkali metal, a group $SO_2R''$ in which R'' is a phenyl or tolyl group; or an acrylic, methacrylic, vinyl or allylic polymerizable group optionally containing a long chain; H is a 4- to 7-membered and preferably 5- or 6-membered aromatic heterocycle or an aromatic hydrocarbon-based ring, the heterocycle containing one or more endocyclic hetero atoms chosen from nitrogen, oxygen and sulfur, it being possible for these rings and heterocycles to be substituted with one or more groups as defined for $R_2$ and $R_3$, fused with an aromatic or cycloalkyl ring.

15. The transparent solid material of claim 14, further defined as comprising 0.01 to 20% by weight of photochromic compounds.

16. The transparent solid material of claim 14, further comprising a second photochromic compound to give rise to different colorations.

17. A transfer varnish comprising a photochromic compound of formula:

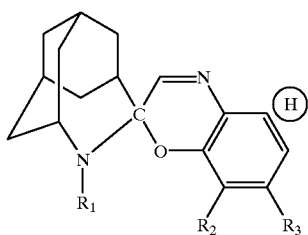

in which:

- $R_1$ represents a $C_1$–$C_{16}$ alkyl group optionally substituted with one or more hydroxyl, halogen, aryl, alkoxy, acyloxy, acryloxy, methacryloxy or vinyl substituents; a vinyl, allyl, phenyl or arylalkyl group, a phenyl group mono- or disubstituted with $C_1$–$C_6$ alkyl or alkoxy or halogen substituents, an optionally substituted alicyclic group, or an aliphatic hydrocarbon group containing in its chain or more hetero atoms chosen from O, N and S;
- $R_2$ and $R_3$ denote, independently of each other, a hydrogen atom; an alkyl group; an aryl group; a group —$(CH_2)_m OR$, —SR, —COR or —COOR, in which R denotes a hydrogen atom, an alkyl group or an aryl group and m is an integer from 0 to 10; an amino group of formula $NR_4R_5$ in which $R_4$ and $R_5$ denote, independently of each other, a hydrogen atom, an alkyl group, a cycloalkyl group, an aryl group, it being possible for $R_4$ and $R_5$ to form, with the nitrogen atom, a 4- to 7-membered heterocycle which can also contain one or more endocyclic hetero atoms chosen from nitrogen, oxygen and sulfur; a halogen atom; a mono- or polyhaloalkyl group; an —$NO_2$, —CN or —SCN group; a group $SO_3R'$ in which R' denotes hydrogen or an alkali metal, a group $SO_2R''$ in which R'' is a phenyl or tolyl group; or an acrylic, methacrylic, vinyl or allylic polymerizable group optionally containing a long chain; H is a 4- to 7-membered and preferably 5- or 6-membered aromatic heterocycle or an aromatic hydrocarbon-based ring, the heterocycle containing one or more endocyclic hetero atoms chosen from nitrogen, oxygen and sulfur, it being possible for these rings and heterocycles to be substituted with one or more groups as defined for $R_2$ and $R_3$, fused with an aromatic or cycloalkyl ring.

* * * * *